United States Patent [19]

Wermuth et al.

[11] Patent Number: 4,710,289

[45] Date of Patent: Dec. 1, 1987

[54] CHROMATOGRAPHY PRECOLUMN

[75] Inventors: Stefan Wermuth, Darmstadt; Günter Hauke, Mühltal; Klaus Kreher, Münster, all of Fed. Rep. of Germany

[73] Assignee: Merck Patent Gesellschaft mit beschrankter Haftung, Darmstadt, Fed. Rep. of Germany

[21] Appl. No.: 19,737

[22] Filed: Feb. 27, 1987

[30] Foreign Application Priority Data

Feb. 28, 1986 [DE] Fed. Rep. of Germany ....... 3606474

[51] Int. Cl.$^4$ .............................................. B01D 15/08
[52] U.S. Cl. ................................... 210/198.2; 55/386
[58] Field of Search ................ 210/198.2, 656; 55/386

[56] References Cited

U.S. PATENT DOCUMENTS

| 3,511,377 | 5/1970 | Hrdina | 210/198.2 |
|---|---|---|---|
| 3,855,130 | 12/1974 | Randau | 210/198.2 |
| 4,280,905 | 7/1981 | Gunkel | 210/198.2 |
| 4,283,280 | 8/1981 | Brownlee | 210/198.2 |
| 4,309,286 | 1/1982 | Lenihan | 210/198.2 |
| 4,510,058 | 4/1985 | Cais | 210/198.2 |
| 4,554,071 | 11/1985 | Ruijten | 210/198.2 |
| 4,636,316 | 1/1987 | Harris | 210/198.2 |
| 4,655,917 | 4/1987 | Shackelford | 210/198.2 |

FOREIGN PATENT DOCUMENTS

| 2626946 | 12/1977 | Fed. Rep. of Germany ... 210/198.2 |
|---|---|---|
| 2930962 | 2/1981 | Fed. Rep. of Germany ... 210/198.2 |
| 3,021,306 | 12/1981 | Fed. Rep. of Germany ... 210/198.2 |
| 3,143,075 | 5/1983 | Fed. Rep. of Germany ... 210/198.2 |

Primary Examiner—Ernest G. Therkorn
Attorney, Agent, or Firm—Millen & White

[57] ABSTRACT

The application relates to a precolumn for a chromatography column in cartridge from which is packed with a sorbent and has been provided with frit and sealing elements, the precolumn being composed of an outer holder and, emplaceable therein, an inner sorbent-packed column ring.

2 Claims, 2 Drawing Figures

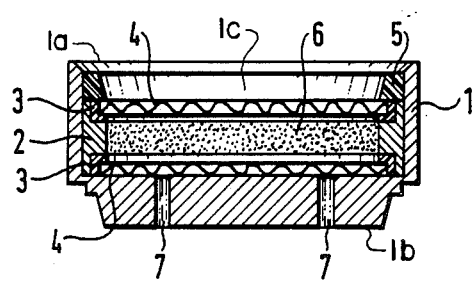
Fig.1
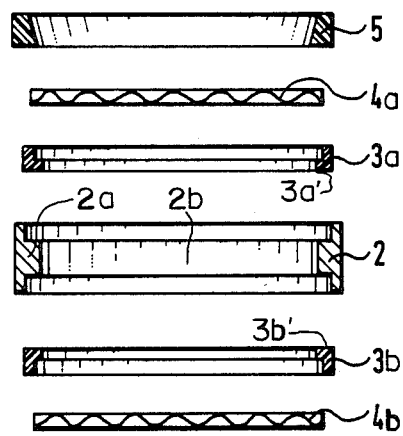
Fig.2
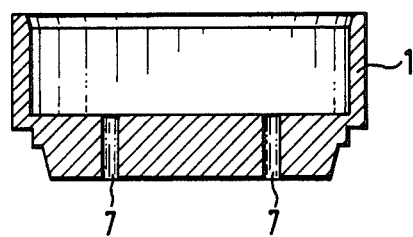

4,710,289

CHROMATOGRAPHY PRECOLUMN

BACKGROUND OF THE INVENTION

This invention relates to a precolumn for a chromatography column in cartridge form which is packed with sorbent and has been provided with frit and sealing elements.

The chromatography columns used, in particular for high pressure liquid chromatography, are in general stainless steel column tubes which have been provided at both ends with screw fittings and capillary connection points for introducing and discharging eluent.

Of late, there has been a trend towards using column cartridges which have no screw fittings, but where the sorbent-packed column tube, which is sealed with frit and sealing elements, is clamped either in a cartridge holder as described for example in DOS No. 2,930,962, DOS No. 3,021,306 or U.S. Pat. No. 4,283,280, or in a column-clamping device as described in DOS No. 3,143,075. To protect the actual separat-separating column from soiling and blocking, frequently a generally very short precolumn is additionally inserted upstream thereof.

These precolumns are generally made of the same material and with the same diameter as the separating column and, like the latter, are provided with frit elements and seals, i.e., are thus constructed like the separating columns themselves, except for the fact that the precolumns are much shorter.

Since the precolumns, on account of their function, serve as traps for soil particles and contaminants which are bonded irreversibly to the sorbent and therefore must frequently be replaced, their elaborate and costly finish leads to a considerable financial burden on the user.

On the other hand, however, the precolumn must meet the same high requirements concerning stability, pressure load limit, tightness and dimensional accuracy as the separating column itself, so that in this area, despite the need for a less costly design of precolumns, no savings in terms of material and finish appeared possible.

SUMMARY OF THE INVENTION

It has now been found, however, that by dividing the precolumn into an outer holder and, emplaceable therein, a column ring, the problem with prior art precolumns can be solved.

The invention accordingly provides a precolumn for a chromatography column in cartridge form which is packed with a sorbent and has been provided with frit and sealing elements, characterized in that the precolumn is composed of an outer holder and, emplaceable therein, an inner sorbent-packed column ring.

BRIEF DESCRIPTION OF THE DRAWINGS

Various other objects, features and attendant advantages of the present invention will be more fully appreciciated as the same becomes better understood when considered in connection with the accompanying drawings, in which like reference characters designate the same or similar parts throughout the several views, and wherein:

FIG. I is a section through a sorbent-packed precolumn; and

FIG. II shows in section the individual components of a precolumn according to the invention in the form of an exploded view.

DESCRIPTION OF THE PREFERRED EMBODIMENT

In the drawings, 1 signifies the outer holder or casing and 2 the column ring. The numeral 3 identifies seals and 4 identifies frit elements. The numeral 5 is a sealing ring; 6 is the sorbent, and 7 identifies holes for letting through the eluent.

The precolumn according to the invention, like known precolumns, is directly emplaced on a separating column (not shown in the drawings). For this purpose, that side of the precolumn which faces the separating column is customarily constructed in such a way that the side sealingly interacts with the sealing elements which are on the separating column. In the same way, that side of the precolumn which faces the reducing screw fitting with capillary connection points, or the cartridge end screw fitting, is equipped in such a way with sealing elements that a seal is obtained with the conical end of the reducing screw fitting or the cartridge and screw fitting. This known principle is also employed in the precolumn according to the invention, so that, thus, preferably the first end 1a of the precolumn which is uppermost in the drawing is constructed analogously to the upper end of the separating column and the second end 1b of the precolumn which is lowermost in the drawing is constructed analogously to the lower end of the reducing screw fitting or cartridge end screw fitting.

The crucial advantage of the precolumn according to the invention over customary precolumns, however, is that, when a replacement of the precolumn becomes necessary, it is not necessary to renew the complete precolumn, but only the column ring (2) with the seals (3) and frit elements (4) which contain the sorbent (6). This replacement can be easily carried out by the user himself. After removal of the sealing ring (5), the column ring (2) which is inserted into the outer holder (1) can be removed without difficulty. After insertion of a column ring (2) packed with fresh sorbent and after removal of the sealing ring (5), the precolumn is again ready for use. To be able to store and handle a sorbent-packed column ring (2) without problems, the column ring is preferably sealed with seals (3) and frit elements (4).

Thus, the user need acquire the outer holder (1), which must be constructed relatively elaborately in terms of stability, dimensional accuracy and material analogously to the known precolumns, only once, and need budget only for the relatively inexpensive column ring (2) as an item of consumption.

The precolumn according to the invention can be constructed in any desired lengths and diameters, and in this respect is totally adapted to the separating column. Customary dimensions are for example diameters of a few millimeters up to 50–100 cm or more in the case of preparative columns. The lengths of the precolumn can likewise be freely chosen and is in general such that the sorbent packing (6) has a depth of about 10–100 mm.

The precolumn according to the invention is constructed from the materials which are likewise used for separating columns and the customary precolumns. For instance, the outer holder (1) and the column ring (2) are constructed in particular from stainless steel, while the seals (3) and the sealing ring (5) are preferably constructed from inert polymers such as, for example, PTFE, and the frit elements (4) can be made of a sinter metal, such as stainless steel, ceramic or fabric. The sorbent material is conventional and may for example be silica gel or chemically modified silica gel.

Considering the illustrated structure more particularly, the outer holder 1 is in the form of an angular casing defining a circular chamber 1c of a selected internal diameter. The casing 1 has first and second ends 1a and 1b, respectively, with the first end being completely open to accommodate the end of a chromatography column (not shown) and the second end 1b being enclosed by a wall 1c with the openings 7 therethrough for admitting eluent. First and second frit elements 4a and 4b are received in the circular chamber 1c. The first frit element 4a is in abutment with the wall 1b while the second frit element 4c is axially spaced from the wall. Each of the frit elements has a diameter less than that of the circular chamber 1c.

First and second annular sealing members 3a and 3b are provided to retain the frit elements 4a and 4b. The first and second annular sealing members 3a and 3b each have an internal diameter approximating that of the frit elements 4a and 4b, an external diameter less than that of the circular chamber 1c and shoulders 3a' and 3b' each with an internal diameter less than that of the frit elements.

The column ring 2 has an external diameter approximate the internal diameter of the circular chamber 1c and an internal diameter approximate the external diameter of the annular sealing members 3a and 3b. The retaining ring 2 further has an internal annular shoulder 2a spaced from the axial edges thereof a distance equal to the axial dimension of the sealing members 3a and 3b, whereby the sealing members nest between the respective frits 4a and 4b and the column ring 2, while the column ring nests within the circular chamber 1c. A space 2b is defined by the shoulder 2a and the axial space between the frits, which space 2b retains the sorbent material 6.

The elastic sealing ring 5 is disposed in the circular space adjacent the first end of the outer annular casing 1 for effecting a seal between the precolumn and the chromatography column. Preferably, the elastic sealing ring 5 has a frusto-conical inner surface.

Hence an advantageous new precolumn is available for chromatography.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A precolumn for use with a chromatography column, the precolumn comprising:

an outer annular casing defining a circular chamber of a selected internal diameter, having first and second ends with the first end being completely open to accommodate the end of the chromatography column and the second end being enclosed by a wall with openings therethrough for admitting eluent;

a first and a second frit element received in the circular chamber; the first frit element being in abutment with the wall, the second frit element being axially spaced from the wall; each first frit element having a diameter less than that of the chamber;

first and second annular sealing members having internal diameters approximately that of the frit elements, external diameters less than that of the circular chamber and a shoulder with an internal diameter less than that of the frit elements;

a column ring having an external diameter proximate the internal diameter of the circular chamber and an internal diameter proximate the external diameter of the annular sealing members, the ring further having an internal annular shoulder spaced from the edges thereof a distance equal to the axial dimension of the sealing members, whereby the sealing members nest between the respective frits and the column ring while the column ring nests within the circular chamber with a space defined by the shoulder between the frits;

a bed of sorbent disposed in the space defined by the shoulder projecting from the column ring and retained between the first and second frits, and an elastic sealing ring disposed in the circular space between the second end of the outer annular casing for effecting a seal between the precolumn and the chromatography column.

2. The precolumn of claim 1, wherein the outer annular casing is made of stainless steel.

* * * * *